(12) United States Patent
Johnson et al.

(10) Patent No.: US 8,075,599 B2
(45) Date of Patent: Dec. 13, 2011

(54) ADJUSTABLE BONE ANCHOR ASSEMBLY

(75) Inventors: Chris E. Johnson, Germantown, TN (US); Heather Lindenman, Germantown, TN (US); Rodney R. Ballard, Arlington, TN (US); John R. Dimar, Louisville, KY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1519 days.

(21) Appl. No.: 11/253,046

(22) Filed: Oct. 18, 2005

(65) Prior Publication Data

US 2007/0088357 A1    Apr. 19, 2007

(51) Int. Cl.
*A61B 17/70* (2006.01)

(52) U.S. Cl. ........ 606/266; 606/246; 606/264; 606/269; 606/270

(58) Field of Classification Search .......... 606/364, 606/365, 246–278, 70–71, 280–299
See application file for complete search history.

(56) References Cited

U.S. PATENT DOCUMENTS

| | | | |
|---|---|---|---|
| 4,946,458 A | 8/1990 | Harms et al. | |
| 5,190,543 A | 3/1993 | Schlapfer | |
| 5,499,983 A | 3/1996 | Hughes | |
| 5,520,689 A | 5/1996 | Schlapfer et al. | |
| 5,536,268 A | 7/1996 | Griss | |
| 5,562,661 A | 10/1996 | Yoshimi et al. | |
| 5,672,176 A | 9/1997 | Biedermann et al. | |
| 5,716,356 A | 2/1998 | Biedermann et al. | |
| 5,885,286 A | 3/1999 | Sherman et al. | |
| 5,989,254 A | 11/1999 | Katz | |
| 6,030,388 A | 2/2000 | Yoshimi et al. | |
| 6,080,079 A | 6/2000 | Sakai | |
| 6,280,442 B1 * | 8/2001 | Barker et al. | 606/60 |
| 6,296,642 B1 | 10/2001 | Morrison et al. | |
| 6,537,276 B2 | 3/2003 | Metz-Stavenhagen | |
| 6,660,004 B2 | 12/2003 | Barker et al. | |
| 6,692,500 B2 | 2/2004 | Reed | |
| 6,736,820 B2 | 5/2004 | Biedermann et al. | |
| 6,740,086 B2 | 5/2004 | Richelsoph | |
| 6,770,075 B2 | 8/2004 | Howland | |
| 6,800,078 B2 | 10/2004 | Reed | |
| 6,800,079 B2 * | 10/2004 | Reed | 606/266 |
| 6,837,889 B2 | 1/2005 | Shluzas | |
| 7,559,943 B2 | 7/2009 | Mujwid | |
| 7,794,477 B2 * | 9/2010 | Melkent et al. | 606/246 |
| 2002/0026193 A1 | 2/2002 | Barker et al. | |

(Continued)

FOREIGN PATENT DOCUMENTS

DE    4107480    9/1992

(Continued)

*Primary Examiner* — Thomas C. Barrett
*Assistant Examiner* — Matthew Lawson

(57) ABSTRACT

A medical implant device has in one embodiment a receiver member for receiving an elongated member, a crown member, an anchor member and a retaining member. An embodiment of the receiver member has an axial opening, a transverse channel, a chamber including at least one substantially flat wall, and a groove. An embodiment of the crown member has at least one substantially flat side. An embodiment of the anchor member has a head with at least one substantially flat surface that may be parallel to the anchor member's longitudinal axis, and an anchoring portion. An embodiment of the retaining member is a substantially flat clip. The crown member and anchor member are inserted into the chamber, and the retaining member is inserted into the groove beneath them. The anchor member may be pivoted substantially in one plane with respect to the receiver member until locked.

36 Claims, 13 Drawing Sheets

U.S. PATENT DOCUMENTS

| | | |
|---|---|---|
| 2003/0004512 A1* | 1/2003 | Farris et al. .................... 606/61 |
| 2003/0004513 A1* | 1/2003 | Guzman et al. ................. 606/62 |
| 2003/0199873 A1 | 10/2003 | Richelsoph |
| 2004/0172022 A1 | 9/2004 | Landry et al. |
| 2004/0193160 A1 | 9/2004 | Richelsoph |
| 2004/0220575 A1 | 11/2004 | Biedermann et al. |
| 2004/0236330 A1 | 11/2004 | Purcell et al. |
| 2005/0154391 A1 | 7/2005 | Doherty et al. |
| 2005/0159750 A1 | 7/2005 | Doherty |
| 2005/0187548 A1 | 8/2005 | Butler et al. |
| 2005/0261687 A1 | 11/2005 | Garamszegi et al. |
| 2005/0277925 A1* | 12/2005 | Mujwid ........................ 606/61 |
| 2006/0084978 A1* | 4/2006 | Mokhtar ........................ 606/61 |
| 2006/0155277 A1* | 7/2006 | Metz-Stavenhagen ......... 606/61 |
| 2006/0161152 A1* | 7/2006 | Ensign et al. .................. 606/61 |
| 2006/0200131 A1* | 9/2006 | Chao et al. .................... 606/61 |
| 2007/0043355 A1 | 2/2007 | Bette et al. |
| 2007/0090238 A1 | 4/2007 | Justis |
| 2008/0195159 A1 | 8/2008 | Kloss et al. |
| 2008/0306546 A1 | 12/2008 | Zucherman et al. |

FOREIGN PATENT DOCUMENTS

| | | |
|---|---|---|
| DE | 4243951 | 7/1994 |
| DE | 4436262 C1 | 7/1996 |
| DE | 19605640 | 8/1997 |
| DE | 19829699 | 1/2000 |
| EP | 0626828 | 12/1994 |
| WO | 01/15612 | 3/2001 |
| WO | WO/03-096914 | 11/2003 |
| WO | WO/03-096915 | 11/2003 |
| WO | WO/03-096916 | 11/2003 |
| WO | WO 03096915 A1 * | 11/2003 |
| WO | 2006/084443 | 8/2006 |
| WO | WO 2009/106733 | 9/2009 |

* cited by examiner

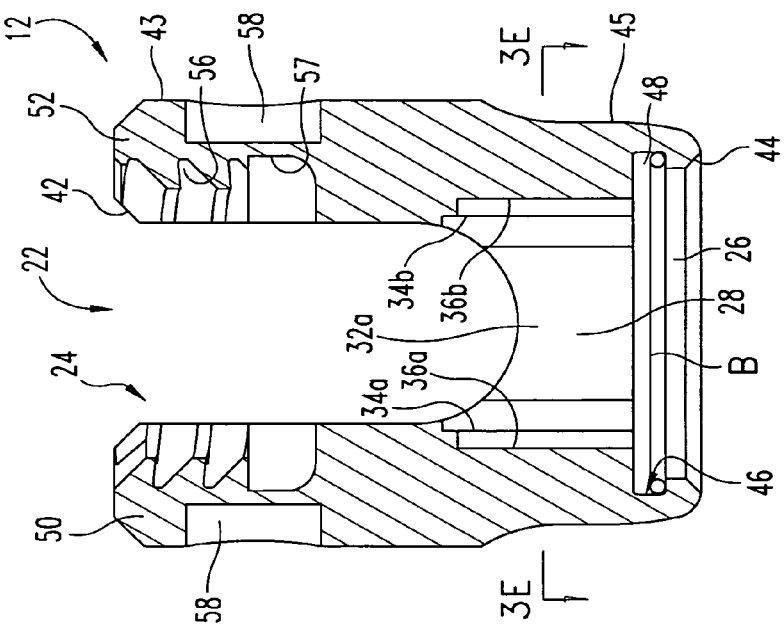
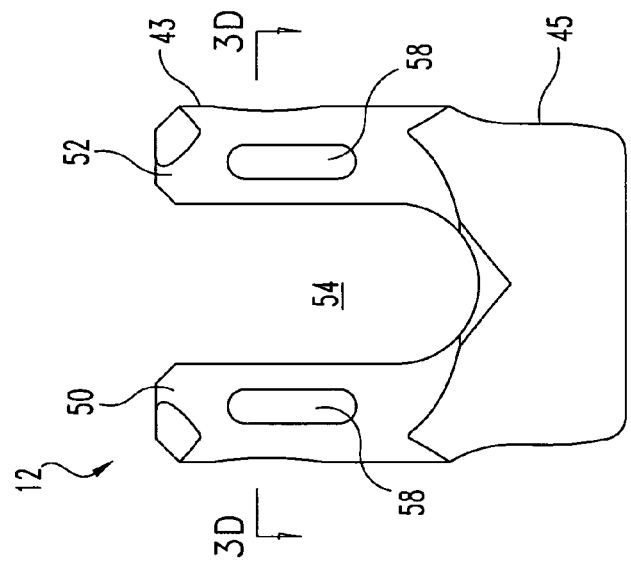
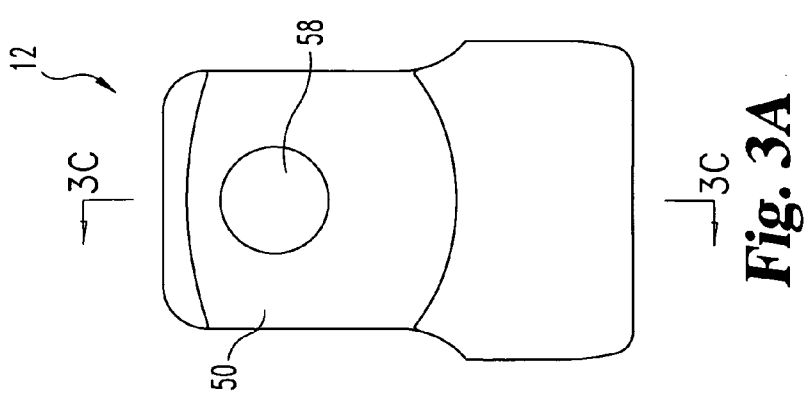

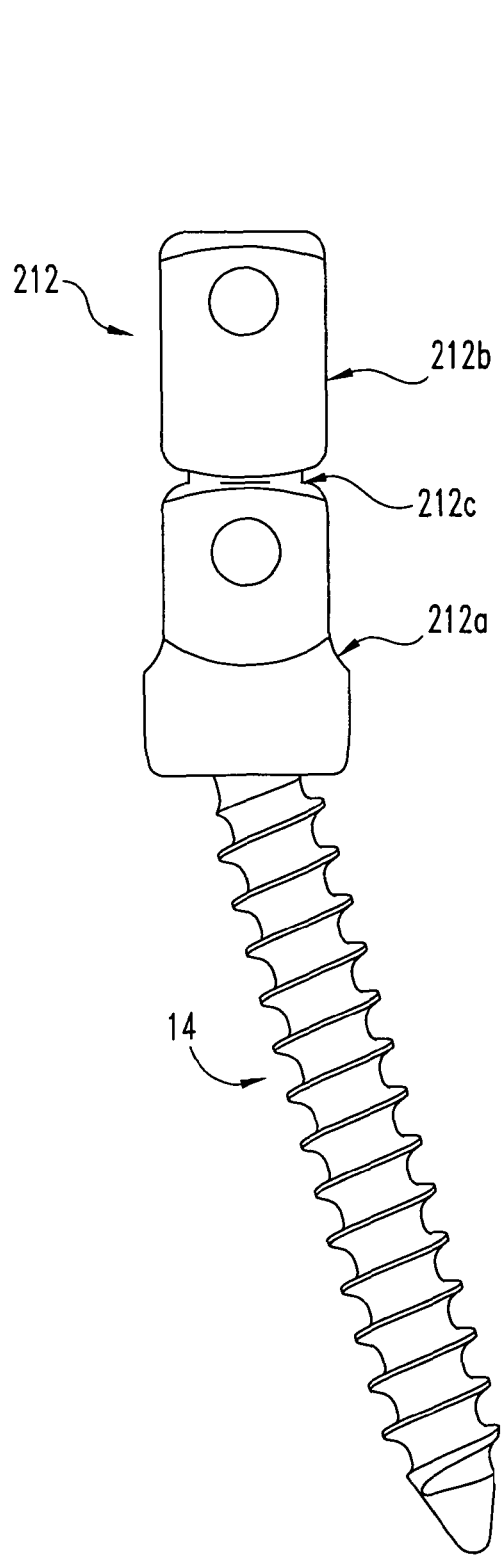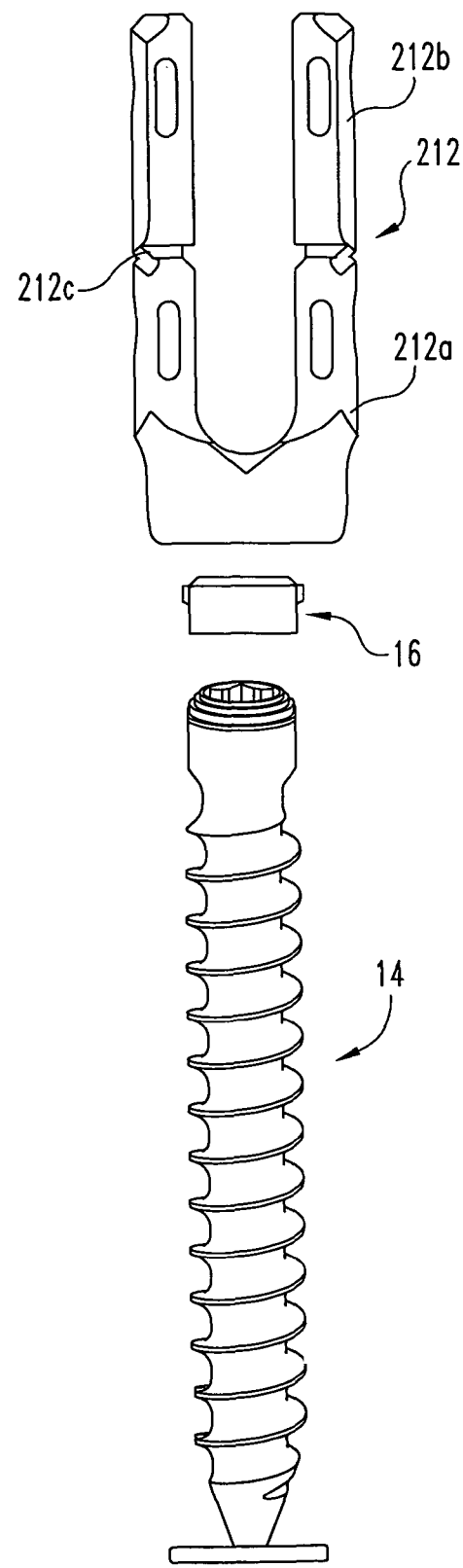
Fig. 9
Fig. 10

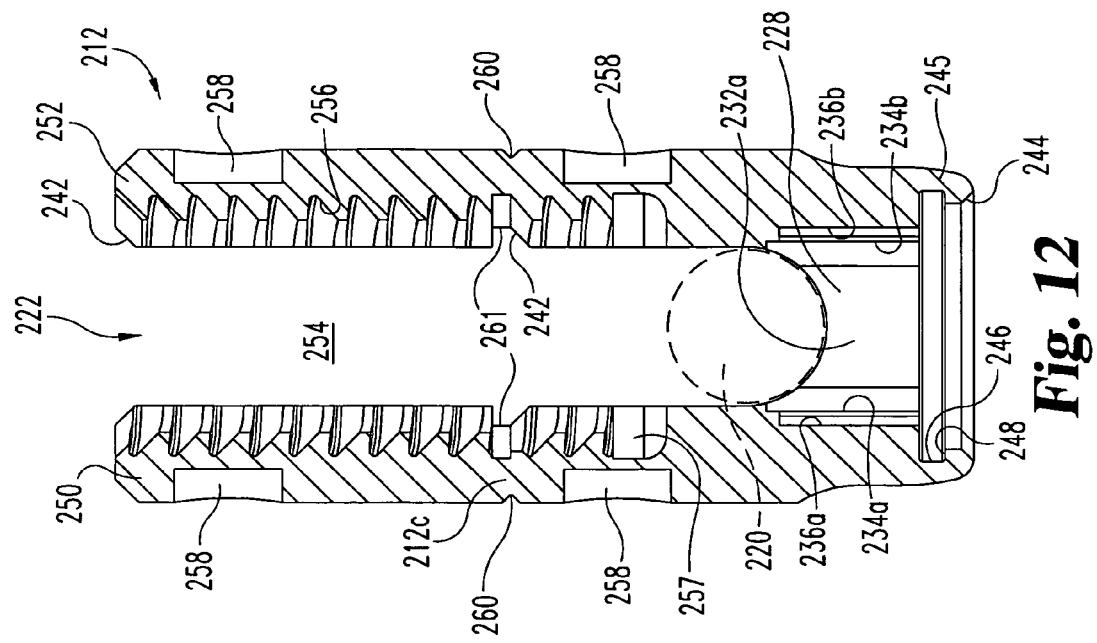
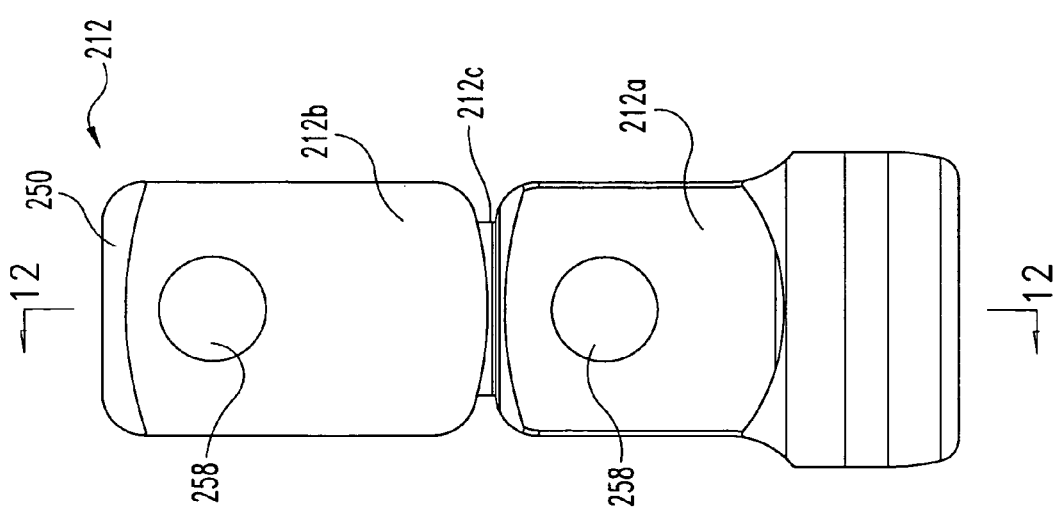

US 8,075,599 B2

ADJUSTABLE BONE ANCHOR ASSEMBLY

The present disclosure relates to devices and methods useful in surgery, such as orthopedic surgery. In particular, it relates to anchors and other implants for use in tissue, to be placed during orthopedic surgery.

In the field of orthopedic surgery, techniques and systems have been developed for correcting and stabilizing damage or malformation of bones, such as the vertebrae of the spine. In one type of system, an elongated member such as a bendable rod is disposed longitudinally along vertebrae or one or more vertebral segments. The rod may be bent to correspond to or approximate the normal curvature of the spine in the particular region being instrumented. For example, the rod can be bent or otherwise formed into at least an approximation of a normal kyphotic curvature for the thoracic region of the spine, or a lordotic curvature for the lumbar region.

In such systems, an elongated member can be engaged to vertebrae along a length of the spinal column by way of a number of fixation elements. A variety of fixation elements can be provided which are configured to engage bones or bony tissue, such as specific portions of a vertebra or other bones. For instance, one such fixation element is a hook that is configured to engage a lamina of a vertebra. Another fixation element is a screw that can be threaded into various parts of the vertebra or other bones.

Such procedures may be used to correct or treat a variety of deformities, injuries or other problems in bony structures such as vertebrae or other tissue. In one example of a spinal procedure utilizing a bendable rod, one or more rods are situated to one or both sides of the spine or spinous processes. Bone screws are threaded into several vertebral bodies, e.g. into the vertebral pedicles. The rods are affixed to the bone screws to apply corrective and/or stabilizing forces to the spine.

BRIEF DESCRIPTION OF THE DRAWINGS

FIG. 3A is a side elevational view of an embodiment of a receiver member shown in FIG. 2.

FIG. 3B is a front elevational view of the embodiment of a receiver member shown in FIG. 3A.

FIG. 3C is a sectional view, taken along the lines 3C-3C in FIG. 3A, and viewed in the direction of the arrows, of the embodiment of a receiver member shown in FIG. 3A.

FIG. 9 is a side elevational view of an embodiment of an adjustable bone anchor assembly.

FIG. 10 is an exploded view of the embodiment depicted in FIG. 9.

FIG. 11 is a side elevational view of an embodiment of a receiver member depicted in FIG. 9.

FIG. 12 is a sectional view, taken along the lines of 12-12 in FIG. 11 and viewed in the direction of the arrows, of the embodiment of a receiver member shown in FIG. 11.

DESCRIPTION OF THE ILLUSTRATED EMBODIMENTS

Figure 1:
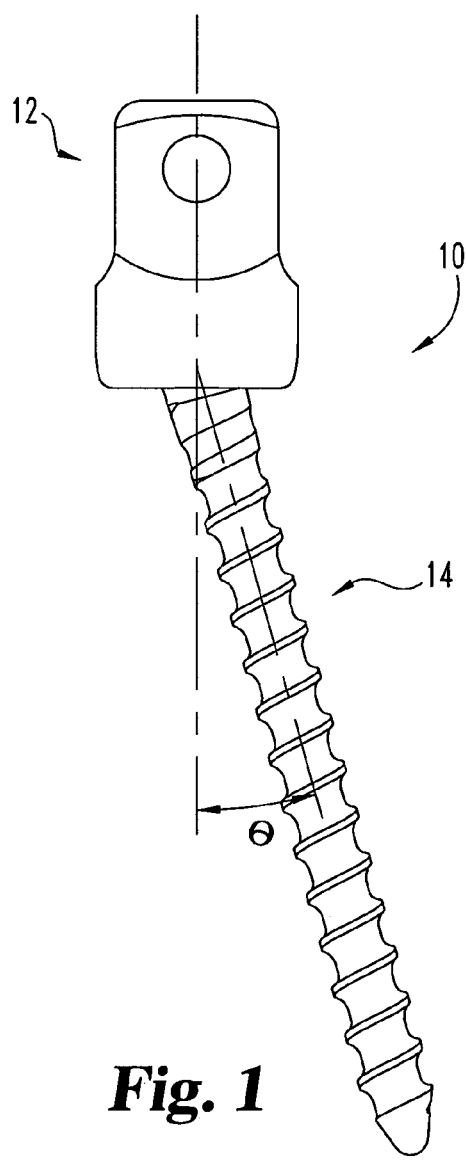
FIG. 1 is a side elevational view of an embodiment of an adjustable bone anchor assembly.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein, being contemplated as would normally occur to one skilled in the art to which the subject matter relates.

Figure 2:
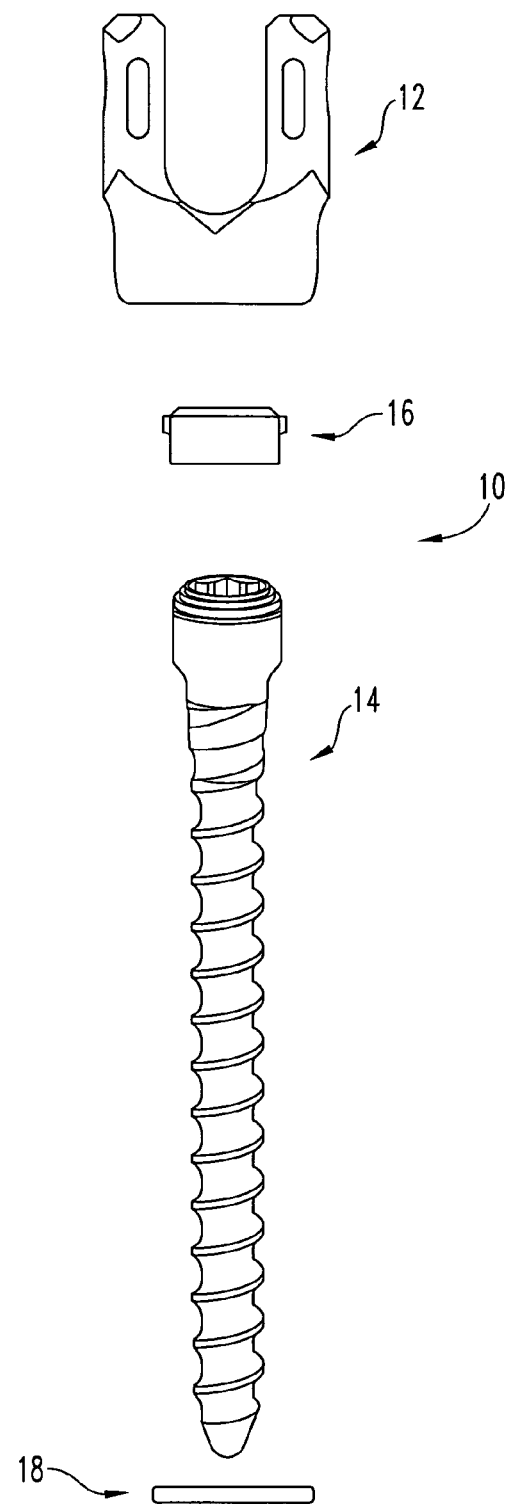
FIG. 2 is an exploded view of the embodiment depicted in FIG. 1.
Figure 3D:
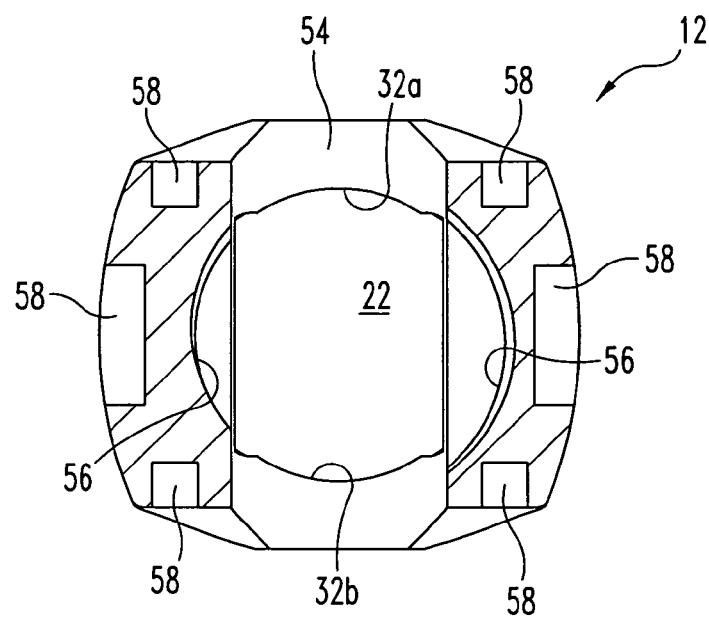
FIG. 3D is a sectional view, taken along the lines 3D-3D of FIG. 3B and viewed in the direction of the arrows, of the embodiment of a receiver member shown in FIG. 3B.
Figure 3E:
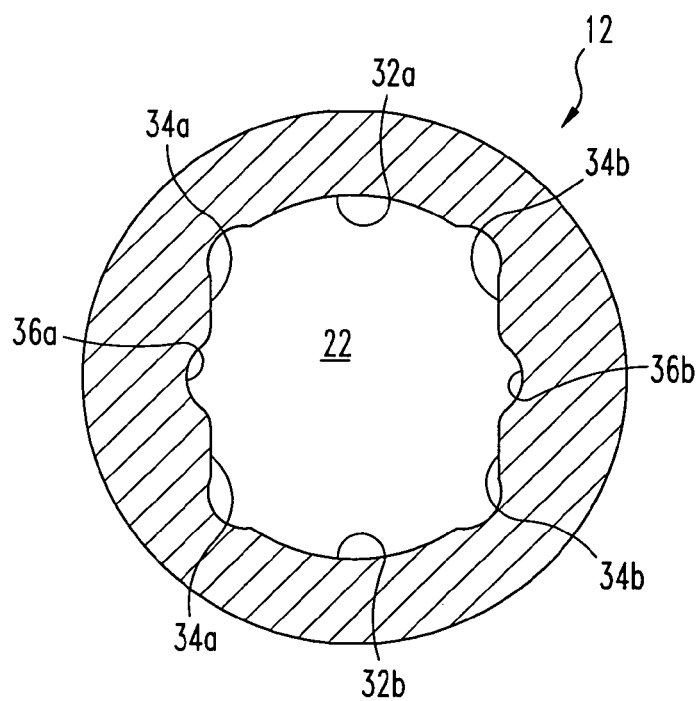
FIG. 3E is a sectional view, taken along the lines 3E-3E of FIG. 3C and viewed in the direction of the arrows, of the embodiment of a receiver member shown in FIG. 3C.

Referring generally to FIGS. 1 and 2, there is shown an embodiment of a bone anchor assembly 10. In that embodiment, assembly 10 includes a receiver member 12, a bone anchor 14, a crown member 16, and a retaining member 18. Assembly 10 is connectable with an elongated member 20 (FIG. 7) such as a spinal rod, pin, bar or other implant construct, as further described below.

Referring now additionally to FIGS. 3A-3E, 7 and 8, an embodiment of the receiver member 12 is shown Receiver member 12 has an axial opening 22 therethrough, which in the illustrated embodiment includes an upper opening portion 24 and a lower opening portion 26. Opening 22 has a longitudinal axis, which in one embodiment is also a longitudinal axis of receiver member 12. Part of opening 22 is a chamber 28. In the illustrated embodiment, chamber 28 has substantially cylindrically-shaped walls or surfaces 32a and 32b and generally flat walls or surfaces 34a and 34b, which may be parallel to each other and to the longitudinal axis of receiver member 12. Walls 34a, 34b may have respective substantially cylindrical wall portions 36a, 36b.

Opening portion 22 is partially surrounded by a chamfered or rounded edge 42 at a top portion 43 of receiver member 12, and is surrounded by chamfered or rounded edge 44 at a bottom portion 45 of receiver member 12. In or adjacent bottom portion 45 of receiver member 12, a groove 46 and associated ledge 48 around lower opening 24 may be provided. In the illustrated embodiment, groove 46 is substantially elliptical or otherwise oval and extends around the entire perimeter of opening 22, although it will be seen that groove 46 could extend only partially around the perimeter of opening 22. Groove 46 has a depth A (FIG. 7), and a major diameter B (FIG. 3C). In the illustrated embodiment, the major diameter of groove 46 is generally parallel to the planes of surfaces 34a, 34b of receiver member 12. Upper and lower opening portions 24, 26 can have a variety of alternative or additional configurations, such as each having one or more sections of differing diameter(s).

Figure 7:
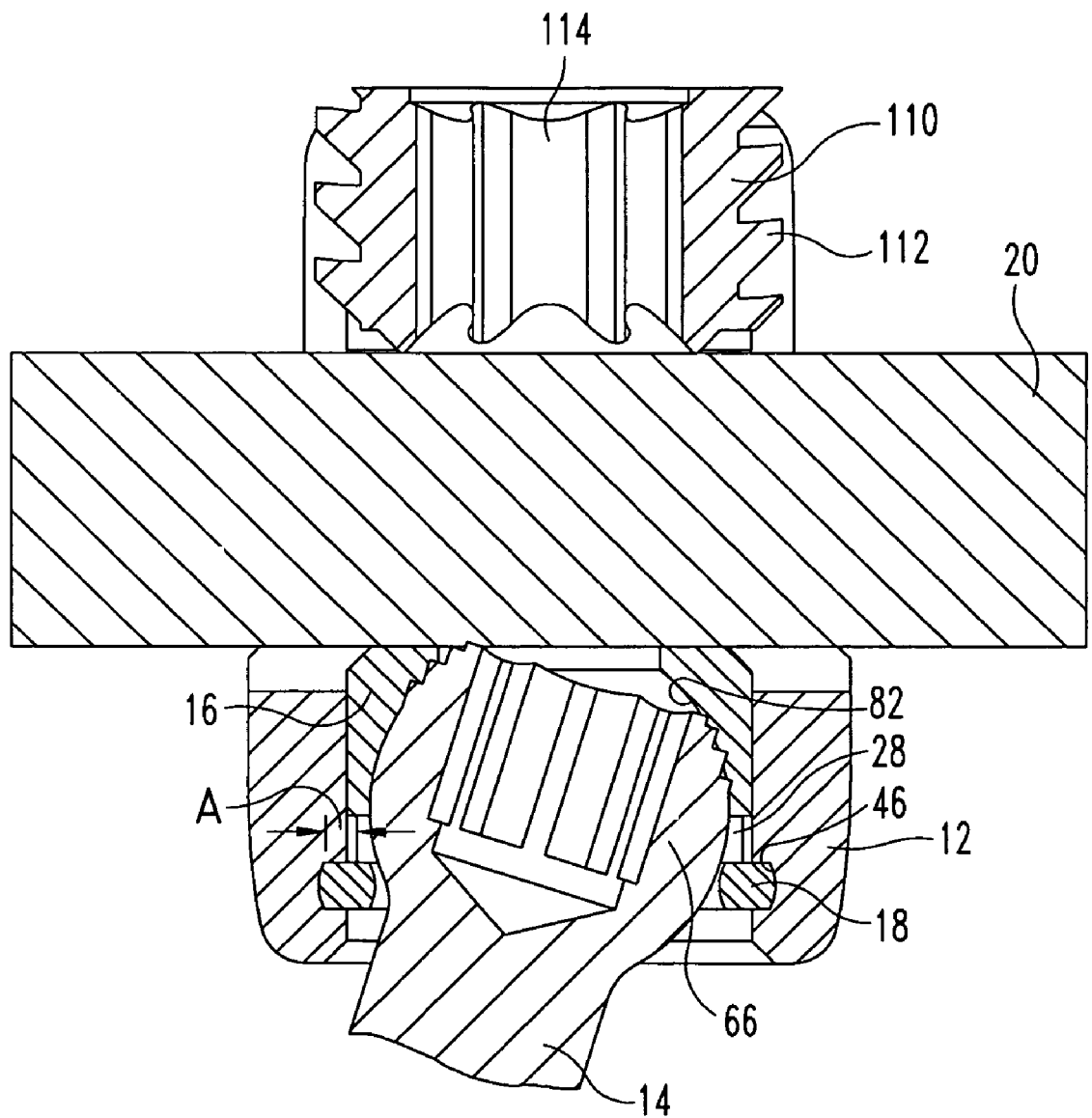
FIG. 7 is an enlarged sectional view of an embodiment as in FIG. 1.
Figure 8:
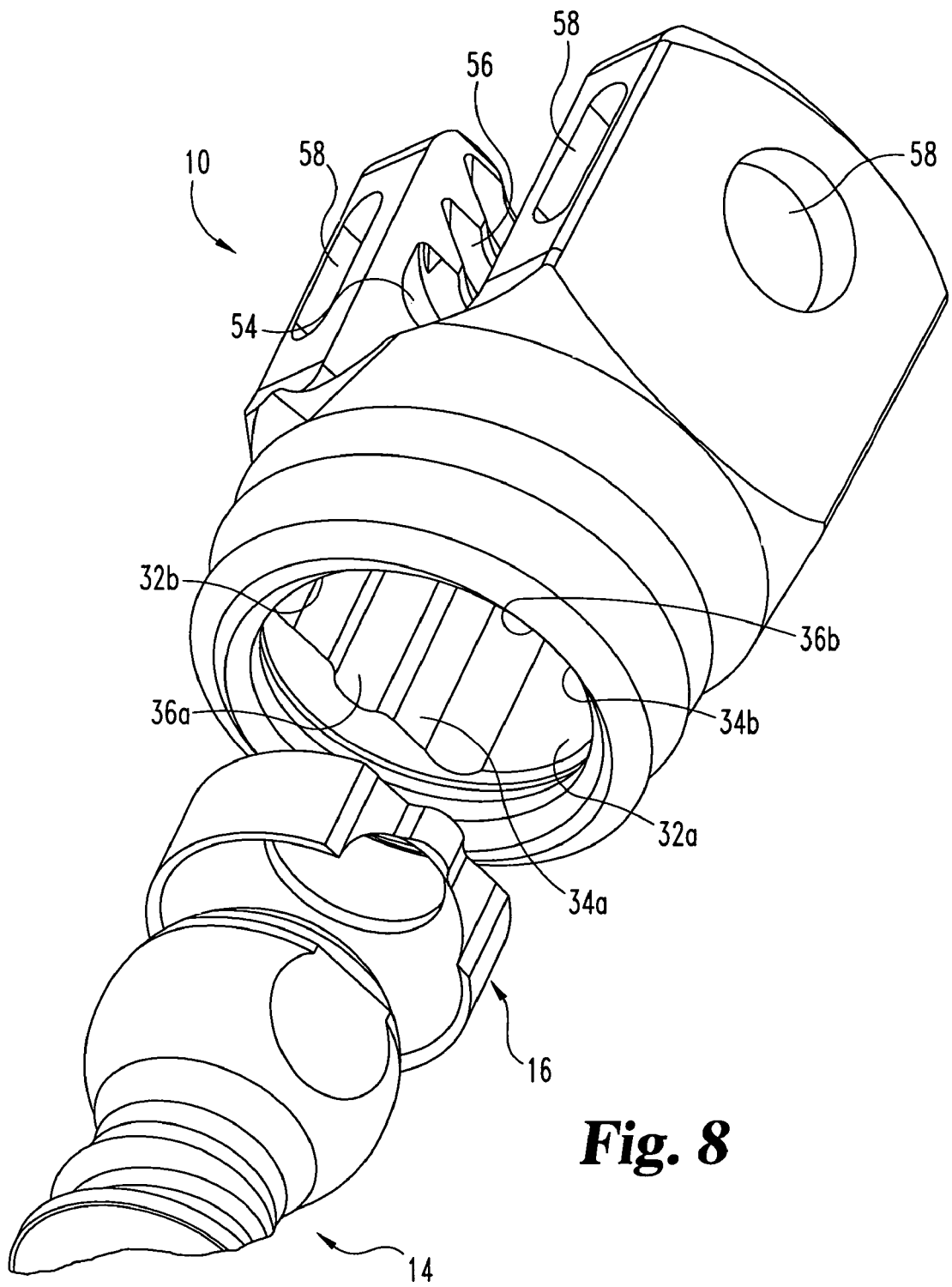
FIG. 8 is an exploded perspective view of an embodiment as in FIG. 7.
Figure 13:
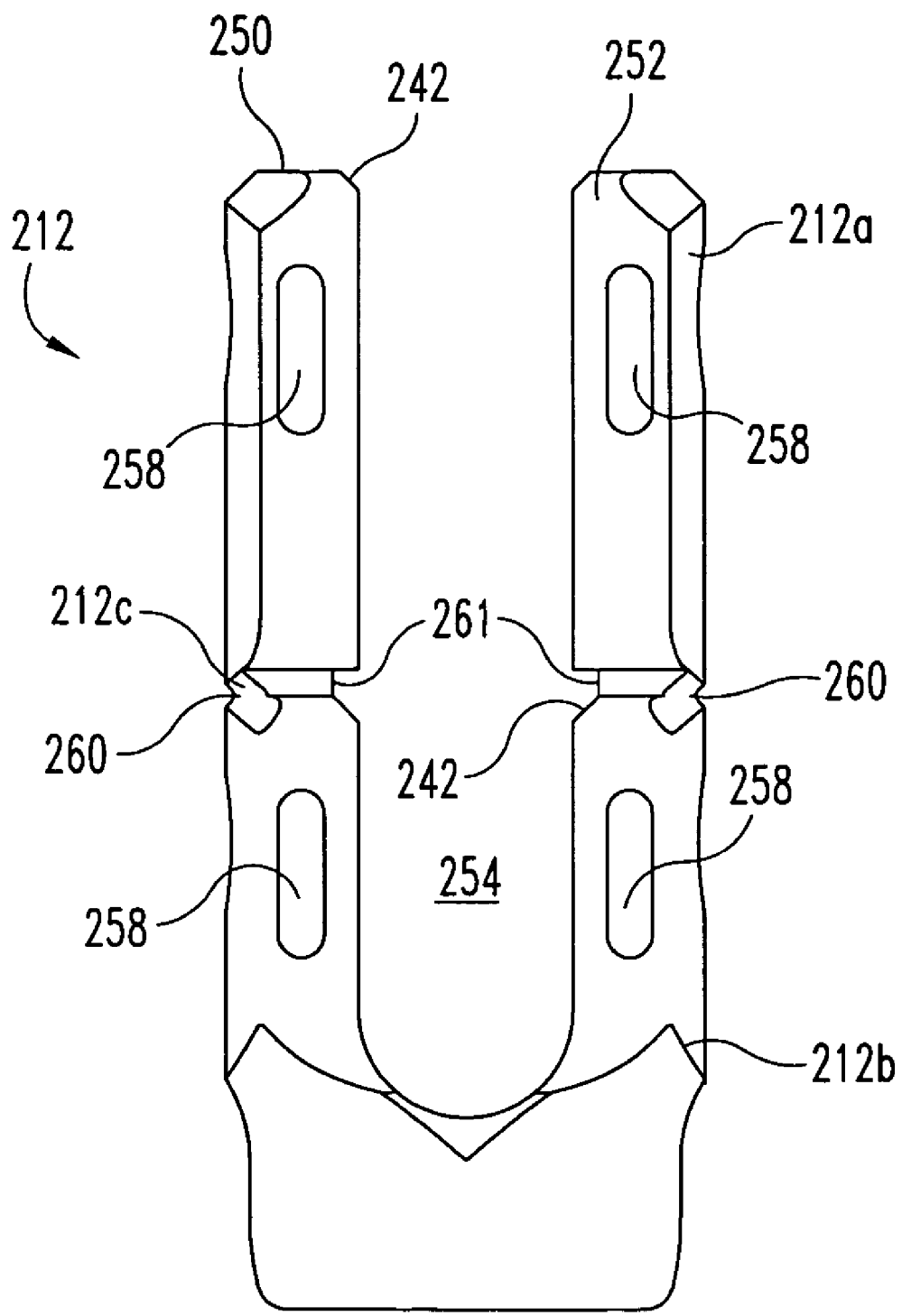
FIG. 13 is a front elevational view of the embodiment of a receiver member depicted in FIG. 9.

Receiver member 12 in the illustrated embodiment includes a pair of upright branches 50, 52 between which opening 22 extends. Branches 50, 52 further define a substantially U-shaped channel 54 transverse to opening 22 that communicates with opening 22, and that is sized to accommodate elongated member 20 (FIG. 7). In a specific embodiment, internal threads 56 may be provided, which end well above the floor of channel 54. If a cylindrical rod 20 of diameter equal to the width of channel 54 is placed in channel 54 as deep as possible, i.e. contacting the floor of channel 54, the upper limit of rod 20 will be below threads 56. A groove 57, which may be slightly larger than the major diameter of threads 56, separates threads 56 from that upper limit of rod 20. Branches 50, 52 may also be provided with indentations or holes 58, which allow the surgeon to grip receiver member 12 with an appropriate forceps, wrench or other gripping or turning tool (not shown). Internal thread 56 in a specific embodiment is a reverse angle thread, i.e. a thread in which a load flank faces down and at lease slightly away from opening 22, as disclosed in commonly-owned U.S. Pat. No. 6,296,642, the disclosure of which is hereby incorporated by reference in its entirety. Top portion 43 of receiver member 12 (which includes some or all of branches 50, 52) is narrower along, channel 54 than bottom portion 45 of receiver member 12 in the illustrated embodiment, which reduces the bulk and profile of receiver member 12.

Figure 4A:
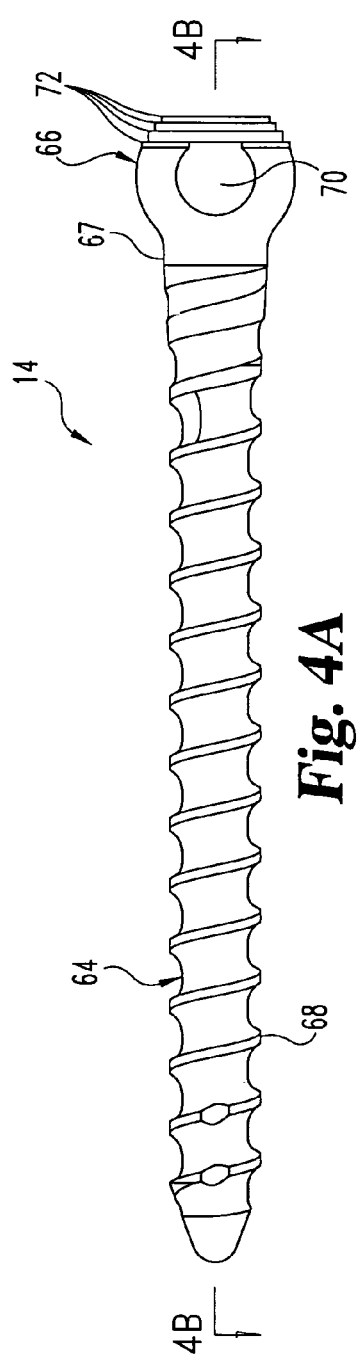
FIG. 4A is a side elevational view of an embodiment of a bone anchor in the embodiment shown in FIG. 2.
Figure 4B:
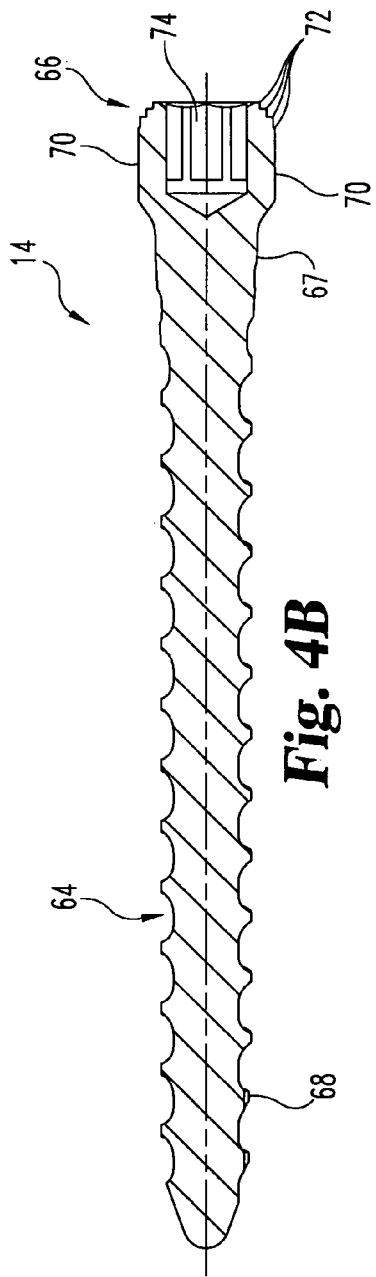
FIG. 4B is a sectional view, taken along the lines 4B-4B of FIG. 4A and viewed in the direction of the arrows, of an embodiment of a bone anchor shown in FIG. 4A.
Figure 4C:
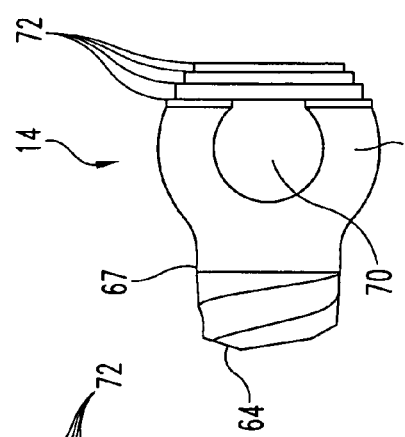
FIG. 4C is a magnified view of an embodiment of a head of a bone anchor shown in FIG. 4A.

Referring now generally to FIGS. 4A-4C, an embodiment of a bone anchor 14 is shown. The illustrated embodiment of bone anchor 14 is a bone screw, which in one embodiment is substantially like the bone screw disclosed in U.S. Pat. No. 5,885,286, the disclosure of which is hereby incorporated by reference in its entirety. Anchor 14 includes an anchorage portion 64 and a head portion 66 joined by a neck or shank portion 67. In the embodiment in which anchor 14 is a screw, anchorage portion 64 includes at least one thread 68, which may be a canceilous self-tapping thread. Head portion 66 forms part of a sphere in the illustrated embodiment, though alternative curvate and other configurations may be employed At least one, and in the illustrated embodiment two, flat surfaces 70 may be provided on opposite sides of-head 66. Head 66, in one particular embodiment, includes a series of ridges 72 for improving purchase with the inside of crown member 16. Head 66 may have alternative or additional friction-increasing surface configuration(s) such as roughening, shot peening or knurling. Further, head 66 can include a tool-engaging print 74, with which a tool (not shown) may be engaged to drive anchorage portion 64 into a bone. Tool-engaging print 74 is an interior print in the illustrated embodiment, although an exterior print could be used, and it may have any of a number of configurations, such as hexagonal, hexalobate, or other torque-transferring configurations. Other embodiments of anchor 14 are contemplated. For example, anchor 14 could be a bone-engaging hook rather than a screw. In that embodiment, anchorage portion 64 would be configured with a hook for engaging tissue, such as a bone portion, rather than a threaded elongated portion.

In one specific example, head 66 has a width between surfaces 70 that is at least slightly smaller than the distance between surfaces 34a, 34b in receiver member 12. The diameter of substantially spherical portions of head 66 is at least slightly smaller than the distance between surfaces 32a, 32b in receiver member 12. Embodiments of head 66 of anchor 14 may be sized to fit in at least lower opening 26 and chamber 28 of receiver member 12. As more fully described below, anchor 14 is inserted into receiver member 12, in one embodiment by inserting head 66 through lower opening portion 26 and into chamber 28 through bottom end 45 of receiver member 12.

Figure 5B:
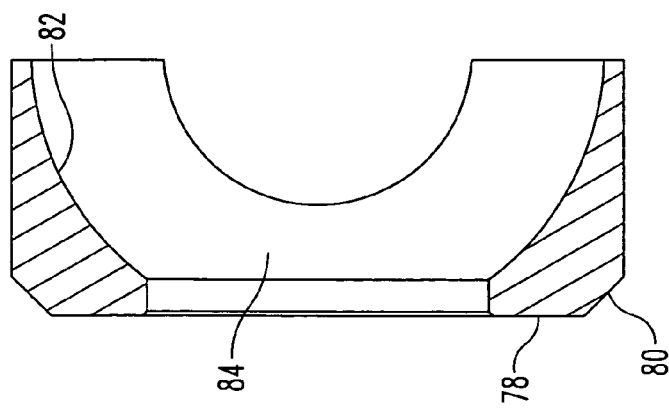
FIG. 5B is a sectional view, taken along the lines 5B-5B in FIG. 5A and viewed in the direction of the arrows, of an embodiment of a crown member shown in FIG. 5A
Figure 5A:
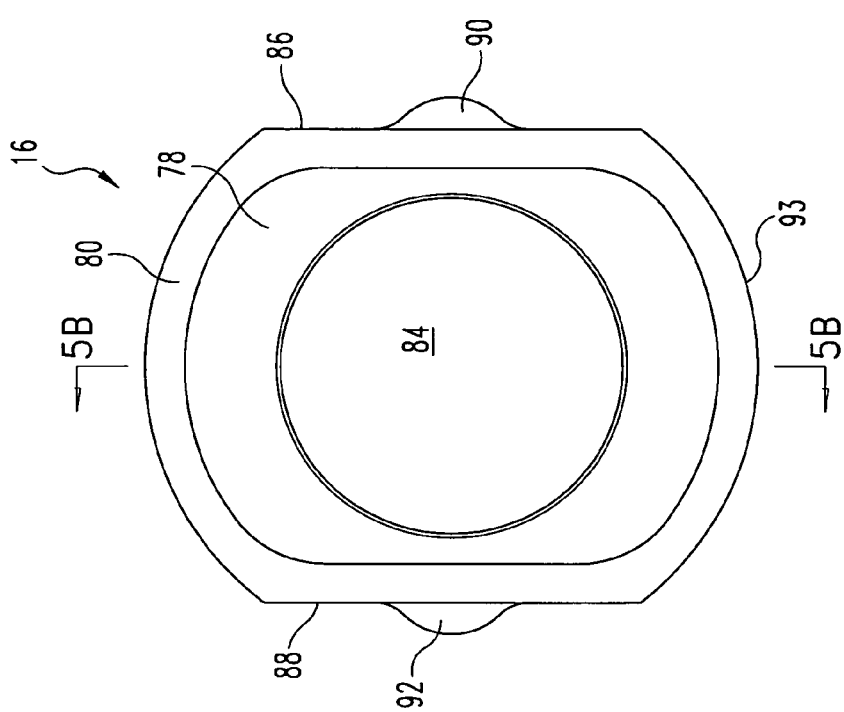
FIG. 5A is a top view of an embodiment of a crown member used in the embodiment shown in FIG. 2.
Figure 5C:
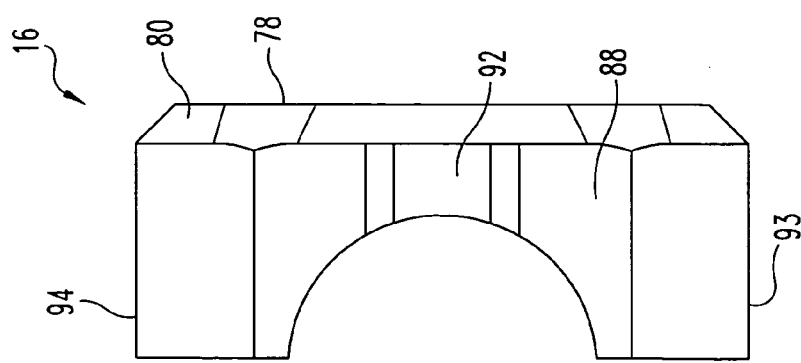
FIG. 5C is a side elevational view of the embodiment shown in FIG. 5k

Referring now to FIGS. 5A-5C, there is shown an embodiment of crown member 16. In that embodiment, crown member 16 is a somewhat oblong disc, having an upper surface 78 with a beveled edge 80 and a lower surface 82. Crown member 16 has a longitudinal central axis L extending thru a bore 84. Bore 84 is sized and configured so that head 66, and specifically tool-engaging print 74, of anchor 14 may be accessed therethrough. Flat side surfaces 86, 88 are provided on opposite sides of crown member 16. Each flat surface 86, 88 has a small rounded protrusion or tab 90, 92, in the illustrated embodiment, extending outwardly from flat surfaces 86, 88 in a direction transverse to longitudinal axis L. Surfaces 93, 94 between surfaces 86, 88 are substantially circular in one embodiment. Lower surface 82 is configured to accommodate head 66 of anchor 14, and in the illustrated embodiment lower surface 82 has the shape of part of a sphere. In other embodiments, lower surface 82 of crown member 16 can have one or more other shapes. Lower surface 82 can be provided with a friction- or purchase-enhancing surface configuration (e.g. roughening or knurling) for cooperation with head 66 of bone anchor 14.

Crown member 16 is sized and shaped to fit in chamber 28 of receiver member 12. The outer dimension of crown member 16 is at least slightly smaller than the inner dimension of chamber 28 so that crown member 16 is slidably movable within chamber 28 in a longitudinal direction. In a particular embodiment, crown member 16 is sized and configured so that sides 86, 88 are adjacent walls 34a, 34b, walls 93, 94 are adjacent walls 32a, 32b, and projections 90, 92 fit at least partially in curved wall sections 36a, 36b of receiver member 12. Crown member 16 and/or lower opening 26 of receiver member 12 may be sized so that crown member 16 may be inserted through lower opening 26 and into chamber 28. Further, in the illustrated embodiment the outer dimension of crown member 16 is larger than the inner dimension of upper opening 24, so that crown member 16 cannot move into the upper opening portion 24 of the receiver member 12. The illustrated embodiment of crown member 16 cannot move fully into channel 54 because of interference between sides 86, 88 and an upper limit of walls 34a, 34b, and/or because of interference between projections 90, 92 and an upper limit of walls 36a, 36b.

Figure 6A:
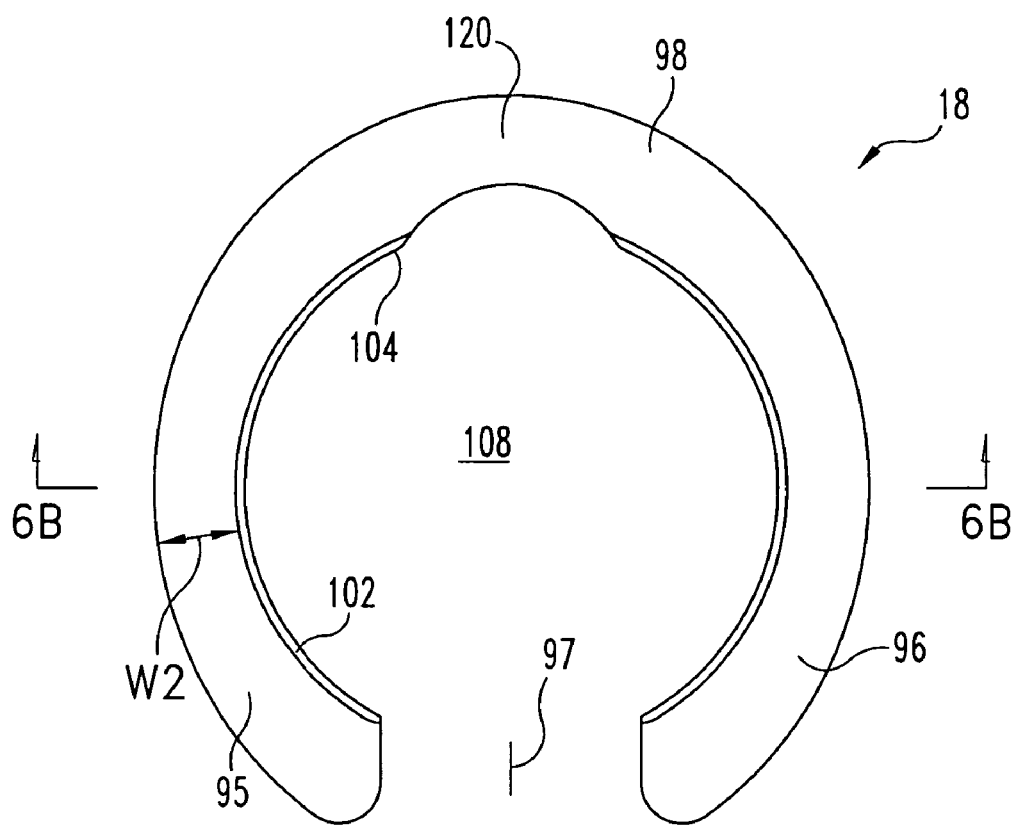
FIG. 6A is a top view of an embodiment of a retaining member used in the embodiment shown in FIG. 2.
Figure 6B:
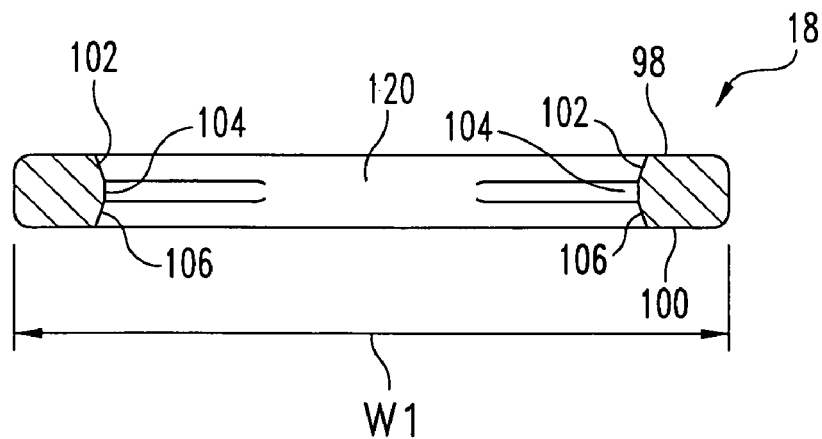
FIG. 6B is a sectional view, taken along the lines of 6B-6B in FIG. 6A and viewed in the direction of the arrows, of an embodiment of a retaining member shown in FIG. 6A.

Referring now to FIGS. 6A-6B, there is shown an embodiment of retaining member or snap ring 18 of the present invention. In the illustrated embodiment, retaining member 18 is substantially C-shaped spring or clip having arms 95, 96 separated by a gap 97. Retaining member 18 includes a top surface 98 and a bottom surface 100. In the illustrated embodiment, retaining member 18 has a substantially elliptical or otherwise oval outer shape, and also includes internal surfaces 102, 104, 106 that substantially surround a substantially circular aperture 108. In other embodiments, there may be single or multiple internal surfaces surrounding aperture 108, which surface(s) may be cylindrical, conical, spherical or of other appropriate configuration, or other inner and/or outer shapes of retaining member 18. In certain embodiments, internal surface 102 forms a portion of a sphere having a radius substantially equal to the radius of head 66 of bone anchor 14, internal surface 104 is substantially cylindrical, and internal surface 106 is substantially conical and angled outward to allow a greater range of angular positioning of anchor 14. Retaining member 18 has an unloaded or natural outer width (e.g. minor width W1 in the elliptic embodiment), i.e. a width measured when retaining member 18 is under no contractive (gap-closing) or expansive (gap-opening) stress. Further, arms 95, 96 of retaining member 18 have a body width W2 which in the illustrated embodiment is greater than depth A of groove 46. The illustrated embodiment of retaining member 18 is further provided with a rotational or hinge area 120, which may be somewhat narrower than W2 or other parts of retaining member 18. The width of retaining member 18, in one embodiment, is less than that of groove 46, e.g. major and minor widths of an elliptic retaining member 18 are less than major and minor diameters of an elliptic groove 46. The diameter of aperture 108 when retaining member 18 is in its unloaded state is smaller than the diameter of head 66 of bone anchor 14. Retaining member 18 may be flat, somewhat wavy or undulating, or otherwise substantially planar in certain embodiments.

Generally referring to FIGS. 1, 2 and 7, assembly 10 is assembled in one embodiment substantially as follows. Bone anchor 14, crown member 16 and retaining member 18 are inserted into receiver member 12 through bottom opening 26, either individually or substantially in one step. As one example, crown member 16 may be inserted first, followed by bone anchor 14 with retaining member 18 being inserted last. With the illustrated embodiments, crown member 16 may be oriented with respect to receiver member 12 and inserted so that its sides 86, 88 are adjacent walls 34a, 34b, walls 93, 94 are adjacent walls 32a, 32b, and projections 90, 92 fit at least partially in curved wall sections 36a, 36b, and so that its underside 82 generally faces lower opening 26 of receiver member 12. Crown member 16 may be slidable along the longitudinal axis of receiver member 12 prior to locking. Head 66 of anchor member 14 may be inserted through lower opening 26 to a position adjacent crown member 16 so that a portion of anchor 14 extends through lower opening 26. A portion of head 66 may be in chamber 28. Retaining member 18 is placed at least partially in groove 46 so that a portion of anchor 14 goes through aperture 108 of retaining member 18. Retaining member 18 may be fitted around anchor 14 just below head 66 prior to, during or after insertion of anchor 14 into receiver member 12. In certain embodiments, retaining member 18 can be placed around anchor 14 by inserting its anchorage portion 64 through aperture 108 and moving retaining member 18 over anchorage portion 64 toward head 66. In other embodiments, gap 97 of retaining member 18 may be pressed against shank or neck 67 of anchor 14 below head 66, so that gap 97 expands and shank 67 moves through gap 97 and into aperture 108, whereupon retaining member 18 may return to its original size and shape. Such expansion of retaining member 18 may be essentially symmetric around -hinge portion 120. By placing crown member 16 adjacent head 66 of anchor 14, so that lower surface 82 of crown member 16 adjoins head 66, and fitting anchor 14 and retaining member 18 together, substantially simultaneous insertion of bone anchor 14, crown member 16 and retaining member 18 into receiver member 12 can be accomplished.

In inserting retaining member 18, it may be forced upward into lower opening portion 26. The surgeon may contract retaining member, making gap 96 smaller, with his or her fingers or other tools, or by forcing retaining member 18 against surfaces 44 and/or 48 of receiving member 12, until the outer width of retaining member I 8 allows its entry into receiver member 12 through lower opening 26. Retaining member 18 is further advanced along opening 22 and into groove 46 so that retaining member 18 extends into at least a portion of groove 46. In embodiments in which retaining member 18 is elliptically shaped, and groove 46 is elliptically shaped, rotation of retaining member 18 about the longitudinal axis of receiver member 12 is limited or prevented by interference of part(s) of retaining member 18 with wall(s) of groove 46.

Notched area 120 of retaining member 18 allows for easy deflection of the arms 95, 96 of retaining member 18 by reducing the force necessary to deflect such arms to close gap 97.

As noted above, in one specific embodiment diameter B of groove 46 is smaller than the outer width W1 of arms 95, 96 of retaining member 18 in its natural or unloaded condition. Thus, when retaining member 18 is in groove 46, retaining member 18 presses against the walls of groove 46. In other embodiments, diameter B of groove 46 may be the same size or slightly larger than the natural outer width W1 of retaining member 18. In this case, the lower surface 100 of retaining member 18 rests upon ledge 48 of groove 46, and thereby holds retaining member 18 within groove 46. Retaining member 18 may be expandable so that arms 95, 96 contact the sides of groove 46 when assembly 10 is assembled and/or locked. Depth A of groove 46 is less than width W2 of retaining member 18, in certain embodiments, so that when retaining member 18 is in groove 46, a portion of retaining member 18 projects into opening 22.

When retaining ring 18 is in groove 46, anchor 14 and crown member 16 are retained within opening 24 of receiver member 12. Crown member 16 is supported by head 66 of anchor 14, and head 66 is supported by retaining member 18 (e.g by internal surface 102, if present). Retaining member 18 is held by groove 46 and/or ledge 48 of receiver member 12. Thus, in this embodiment anchor 14 and crown member 16 do not pass through retaining ring 18 and out of receiver member 12 when retaining ring 18 is within groove 46. Crown member 16 and head 66 of anchor 14 remain positioned in opening 22 and/or chamber 28 of receiving member 12, and are slidable substantially along the longitudinal axis of receiver member 12 prior to locking. Anchor 14 is pivotable in one plane with respect to crown member I 6 and receiving member 12 prior to locking, but in the illustrated embodiment is substantially limited from pivoting or rotating around the longitudinal axis of receiver member 12 because of the relationship between surfaces 70 of anchor 14 and corresponding surfaces of crown member 16 and/or receiver member 12.

Use of the illustrated embodiment of assembly 10 will be described with respect to spinal surgery, but it is understood that assembly 10 could be used in connection with other surgical locations or tissues. Assembly 10 can be used in a variety of surgical procedures, such as those for the correction of deformity (such as a scoliotic curvature, where one or both of translation and rotation of vertebrae or other movement in one or both of coronal and sagittal planes may be required), degeneration or trauma suffered by the spine or other tissues.

Assembly 10 may be assembled prior to use in a surgical procedure, although such assembling could be done by the surgeon, an assistant or another at any time. Anchor 14 is provided at a surgical site and connected to a vertebra (not shown). In the embodiment in which anchor 14 is a screw, it is threaded into the vertebra, for example into a prepared (e.g.

drilled and tapped) hole. In other embodiments, for example where anchor 14 is a bone hook, threading into a bone and/or drilling a hole in the bone may not be necessary. Anchoring portion 64 is connected to the vertebra, and an appropriate turning tool, e.g. one usable with tool-engaging print 74 of anchor 14 through hole 84 in crown member 16, may be used to thread anchor 14 into the bone. When anchor 14 has been inserted or otherwise placed with respect to a vertebra to the desired depth, receiver member 12 can be positioned so that opening 22 forms a desired angle with anchor 14. In the illustrated embodiment, the angle θ between anchor 14 and opening 22 can be any value up to 30 degrees in either direction. It will be seen that the maximum angle of anchor 14 relative to opening 22 can be changed in several ways, for example by thinning the shank or other portion of anchor 14 beneath head 66, by providing a steeper angle of surface 44 relative to the longitudinal axis of receiver member 12, and/or by placing groove 46 as close as possible to bottom end 24 of receiver member 12. The surgeon may line up channel 54 and an elongated member 20 so that they are parallel, and/or may bend the elongated member to enable it to be easily reduced into receiver member 12 and provide the desired support to the vertebra(e). Assembly 10 allows for movement of receiver member 12 with respect to anchor 14 substantially in one plane, for example the sagittal plane, when or before elongated member 20 and channel 54 are aligned. As noted, surfaces 34a, 34b inside chamber 28, outer sides 86, 88 of crown member 16, and surfaces 70 on head 66 of anchor 14 will substantially limit or prevent anchor 14 from rotating with respect to receiver member 12 other than substantially in the plane including the longitudinal axis of anchor 14 and parallel to surfaces 70 of anchor 14.

As noted above, receiver member 12 may be angled with respect to anchor 14. Elongated member 20, which may be a cylindrical, flattened or otherwise shaped orthopedic rod, pin, bar, connector, or other implant, is coupled with assembly 10. Elongated member 20 is placed in channel 54 of receiver member 12, and adjacent top surface 78 of crown member 16. A compression member 110 is connected to receiver member 12, as by threading compression member 110 into threads 56, and engaged with elongated member 20. Compression member 110, in one embodiment, is a set screw or plug having external threads 112 and a print 114 for applying torque, and in a specific embodiment may be a break-off set screw, such as those disclosed in U.S. Pat. No. 5,885,286 to Sherman et al. or U.S. Pat. No. 6,193,719 to Goumay et al., incorporated herein by reference in their entireties. In a further embodiment, thread 112 is a reverse angle thread as disclosed in U.S. Pat. No. 6,296,642 to Morrison et al., incorporated herein by reference in its entirety, which is compatible with a reverse angle embodiment of thread 56 of receiver member 12, described above. In embodiments in which receiver member 12 is externally threaded, compression member 110 could be an internally-threaded nut.

As compression member 110 is tightened, elongated member 20 is forced downward against crown member 16, which pushes crown member 16 against head 66 of anchor 14. Head 66 is thereby clamped between retaining member 18 and crown member 16. In embodiments in which head 66 includes ridges 72, ridges 72 are pressed into lower surface 82 of crown member 16. Head 66 is pressed against retaining member 18 in groove 46. In this way, anchor 14 is locked with respect to elongated member 20 and the remainder of assembly 10 in the desired angular position.

Materials for the components as described above and in other embodiments include stainless steel, cobalt-chrome alloys, titanium or any other sturdy biocompatible material.

In a particular embodiment, crown member 16 may be made of a material somewhat softer than the material used for ridges 72 of head 66 of anchor 14. Such construction will allow ridges 72 to penetrate somewhat more easily into interior surface 82 of crown member 16 during locking of assembly 10, thereby providing a more definite purchase between ridges 72 and crown member 16. In another specific embodiment, crown member 16 may be made of a material somewhat softer than the material used for elongated member 20. Such construction will allow upper surface 78 of crown member 16 to deform to a shape similar to or approximating that of elongated member 20 during locking of assembly 10. In other embodiments, elongated member 20 may be somewhat softer than crown member 16 so that upper surface 78 of crown member 16 bites into, penetrates, or otherwise deforms elongated member 20.

Referring now generally to FIGS. 9-13, there is shown another embodiment of a receiver member 212, which is similar or identical in many respects to the embodiment of receiver member 12. Features of receiver member 212 that are similar or identical to those of receiver member 12 have the same number with a 200 prefix.

Receiver member 212 has a lower portion 212a and an upper portion 212b separated by a thinned section 212c, in this illustrated embodiment. Lower portion 212a is substantially the same as receiver member 12, having an opening 222 therethrough with a longitudinal axis, which in one embodiment is also a longitudinal axis of receiver member 212. Part of opening 222 is a chamber 228, which in the illustrated embodiment has substantially cylindrically-shaped walls or surfaces (such as surface 232a and an opposing surface) and generally flat walls or surfaces 234a and 234b, which may be parallel to each other and to the longitudinal axis of receiver member 212. Walls 234a, 234b may have respective substantially cylindrical wall portions 236a, 236b. A chamfered or rounded edge 242 may be provided at or near the top of lower portion 212a and/or the top of upper portion 212b, and a chamfered or rounded edge 244 may be provided at a bottom portion 245 of lower portion 212a. A groove 246 and associated ledge 248 may also be provided. Groove 246 is configured substantially like groove 46, with shape(s) and dimension(s) as described and suggested above.

Receiver member 212 in the illustrated embodiment includes a pair of upright branches 250, 252 between which opening 222 extends. Branches 250, 252 further define a substantially U-shaped channel 254 transverse to opening 222 that communicates with opening 222, and that is sized to accommodate an elongated member. A portion of each branch 250, 252 forms at least a part of lower portion 212a of receiver member 212, and a portion of each branch 250, 252 forms at least a part of upper portion 212b of receiver member 212. In a specific embodiment, internal threads 256 are formed in branches 250, 252 through substantially the entire length of upper portion 212b and into lower portion 212a. Threads 256, if provided, end well above the floor of channel 254. If a cylindrical rod 220 of diameter equal to the width of channel 254 is placed in channel 254 as deep as possible, i.e. contacting the floor of channel 254, the upper limit of rod 220 will be below threads 256. A groove 257, which may be slightly larger than the major diameter of threads 256, separates threads 256 from that upper limit of rod 220. Branches 250, 252 may also be provided with indentations or holes 258, which allow the surgeon to grip receiver member 212 (or either or-both of portions 212a, 212b) with an appropriate forceps, wrench or other gripping or turning tool (not shown). Threads 256 in a specific embodiment can be a reverse angle thread, i.e. a thread in which a load flank faces down and at lease slightly away from opening 222, as disclosed in commonly-owned U.S. Pat. No. 6,296,642, the disclosure of which is hereby incorporated by reference in its entirety.

Upper portion 212b of receiver member 212 includes portions of branches 250, 252 having internal threads 256 and indentations 258 as discussed above, in the illustrated embodiment. Threads 256 may configured so that they are essentially continuous from upper portion 212b to lower portion 212a, with the possible exception of the portion at or around section 212c. In that embodiment, a compression member (e.g. compression member 110 described above) can be inserted into upper portion 212b and moved down to lower portion 212a. For example, a set screw threaded into upper portion 212b can be threaded along opening 222 into lower portion 212a In the illustrated embodiment, upper portion 212b is integrally formed with lower portion 212a, although in other embodiments portions 212a and 212b can be separately made and joined together, or otherwise formed. Further, the illustrated embodiment shows upper portion 212b to be of a height approximately the same as or slightly less than that of lower portion 212a. Other embodiments of receiver member 212 could include an upper portion 212b having a height that is half or less than that of lower portion 212a, or could include an upper portion 212b having a height that is substantially larger than that of lower portion 212a.

Thinned section 212c, as noted above, separates upper portion 212b and lower portion 212a in the illustrated embodiment. This embodiment of section 212c includes an external indentation or groove 260, which may include scoring lines or other fracture-inducing or fracture-enabling features. An interior indentation 261 is also provided in the illustrated embodiment, which may interrupt threads 256 (if present) and may be somewhat deeper than the major diameter of threads 256. Section 212c has a thickness which is at least slightly less than the overall thickness of branches 250, 252, and in a particular embodiment that thickness is at least slightly less than the thickness of branches 250, 252 measured from a thread trough in a branch to the exterior of that branch.

Receiver member 212 can be assembled substantially as described above with embodiments of an anchor member 14, a crown member 16, and a retaining member 18, such as those similar or identical to the embodiments described above, to make a bone anchor assembly. Further, the assembly made with receiver member 212 can be used in surgery substantially as described above. When the surgeon wishes to insert an elongated member 220 into receiver member 212, he or she need not bend it or use a special reducing tool to insert it into the lower end of a receiving channel. Rather, he or she places a portion of elongated member 220 into channel 254 in upper portion 212b of receiver member 212. A set screw or other compression member (e.g. compression member 110 described above) is inserted into opening 222 above elongated member 220. In the embodiment in which the compression member is a set screw, the set screw is threaded into threads 256, forcing elongated member 220 further down in channel 254. In this way, elongated member 220 is forced all the way through upper portion 212b, into lower portion 212a, and against a crown member and/or anchor member in chamber 228, substantially as described above with respect to assembly 10.

Once the compression member is tightened against elongated member 220 to lock the assembly to the surgeon's satisfaction, upper portion 212b may be cut or sheared off or otherwise removed from lower portion 212a As one example, tool(s) for gripping or turning could be connected to one or both of upper portion 212b and lower portion 212a and torque could be applied to shear or twist the portions apart. As another example, a tool with relatively sharp jaws could be applied to exterior groove 260 to cut off upper portion 212b. Other methods for physically separating upper portion 212a from lower portion 212b may be used. Once separated, upper portion 212b may be removed from the surgical site and discarded.

As will be noted from the above description, certain embodiments provide a bone anchor having a head portion and an anchoring portion that can pivot with respect to each other in substantially one plane, e.g a sagittal plane, a transverse plane, a plane substantially between a sagittal and a transverse plane, or another plane. Such embodiments may be essentially locked against pivoting with respect to each other in other planes by virtue of internal configurations.

As previously noted, the embodiments described above (and others) can be used for a variety of surgical procedures. Another example of such a procedure concerns applications in which a spinal trauma or degenerative condition exists, and one or more assemblies 10 are used in which the receiver member 12, 212 and the anchor 14 can pivot with respect to each other in substantially one plane. In such cases, assembly 10 can be introduced to a surgical site as described herein or otherwise as the surgeon may desire, and inserted into vertebral tissue. In many surgical procedures, the surgeon may prefer to install assembly 10 so that the plane in which receiver member 12, 212 and anchor 14 can pivot with respect to each other is substantially sagittal, substantially vertical, and/or substantially parallel to at least part of the spinal column. It will be understood, of course, that the surgeon may orient assembly 10 as he or she wishes, for example so that the plane in which receiver member 12, 212 and anchor 14 can pivot with respect to each other is non-sagitally oriented.

Once assembly 10 is inserted into a vertebra, it can be threaded into a position that is one-quarter turn (90 degrees) short of its final position with respect to the vertebra. For example, in a situation in which the final position of assembly 10 with respect to a vertebra is to be such that channel 54, 254 points substantially sagitally or receiver member 12, 212 can pivot in substantially a sagittal plane, assembly 10 can be threaded into a vertebra so that it is one-quarter turn dorsal of that final position (e.g. substantially in a lateral plane). In such a pre-final position, movement in the sagittal plane of receiver member 12, 212 with respect to anchor 14 is substantially limited or prevented. Correction techniques useful in addressing trauma and/or degenerative conditions, such as compression, distraction, rotation and/or other adjustments of vertebrae or vertebral segments, can be applied to bones or to assembly 10 (or multiple assemblies 10, if they are used) in such pre-final positions in vertebrae. For example, if compression is desired, the surgeon may press assemblies 10 together with his or her fingers or with a tool (not shown). As another example, if distraction is desired, the surgeon may pull or push apart assemblies 10 with his or her fingers or with a tool (not shown). In either case, force applied to the sides of assemblies 10 will cause a change in relative position between assemblies 10, and will not substantially pivot receiver members 12, 212 of assemblies 10 with respect to their respective anchors 14. An interbody device may be implanted between the adjusted vertebrae so as to maintain the desired spacing between the vertebrae. Such operations on vertebrae, on one or more assemblies 10, or other orthopedic elements may be made as the surgeon desires and/or as dictated by a particular patient's condition.

Once any adjustment of vertebrae has been performed, and the spine or a portion of it is in a position desired by the surgeon, assembly(s) 10 can be driven the final one-quarter turn into their respective vertebrae. Assembly(s) 10 then rest in the final position with respect to the vertebrae desired by the surgeon An elongated member, such as a spinal rod, bar or other item, may be inserted into channel 54, 254 of receiver member 12, 212 of each assembly 10 and locked, substantially as described above. Using embodiments of the above methods and assemblies, the surgeon has in one device an essentially rigid screw in the direction of distraction and compression when needed, and in its final position a pivotable, angularly adjustable screw when a rod or other elongated member is being seated in it. It will be seen that embodiments of the methods described herein using two or more bone anchor assemblies can, as examples, use assembly 10 for each such bone anchor assembly, or can use other types of anchors along with one or more assembly 10.

While the embodiments have been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

Figures 14, 15:
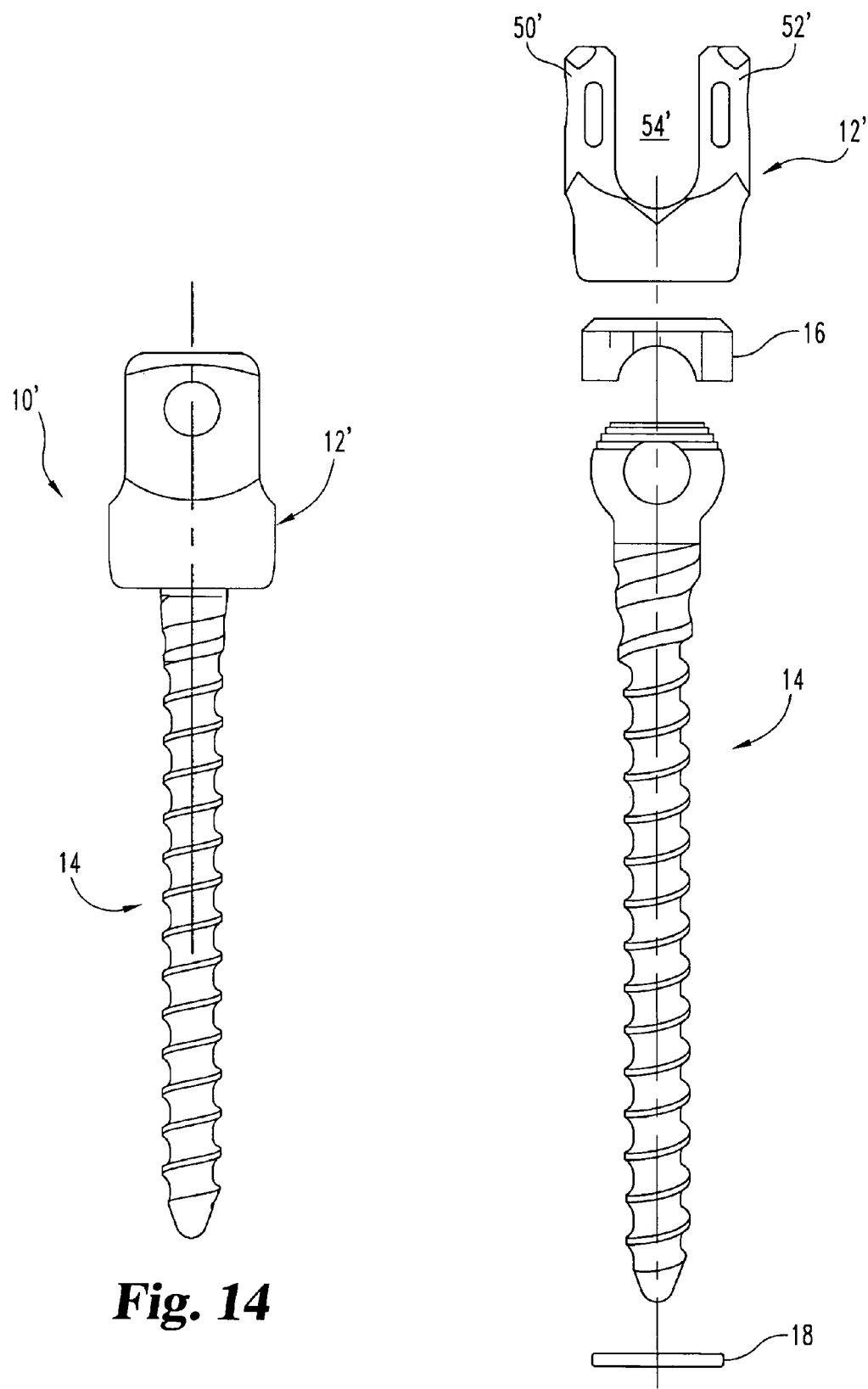
FIG. 14 is an elevational view of an embodiment of an adjustable bone anchor assembly.
FIG. 15 is an exploded view of the embodiment shown in FIG. 14.
Figure 16:
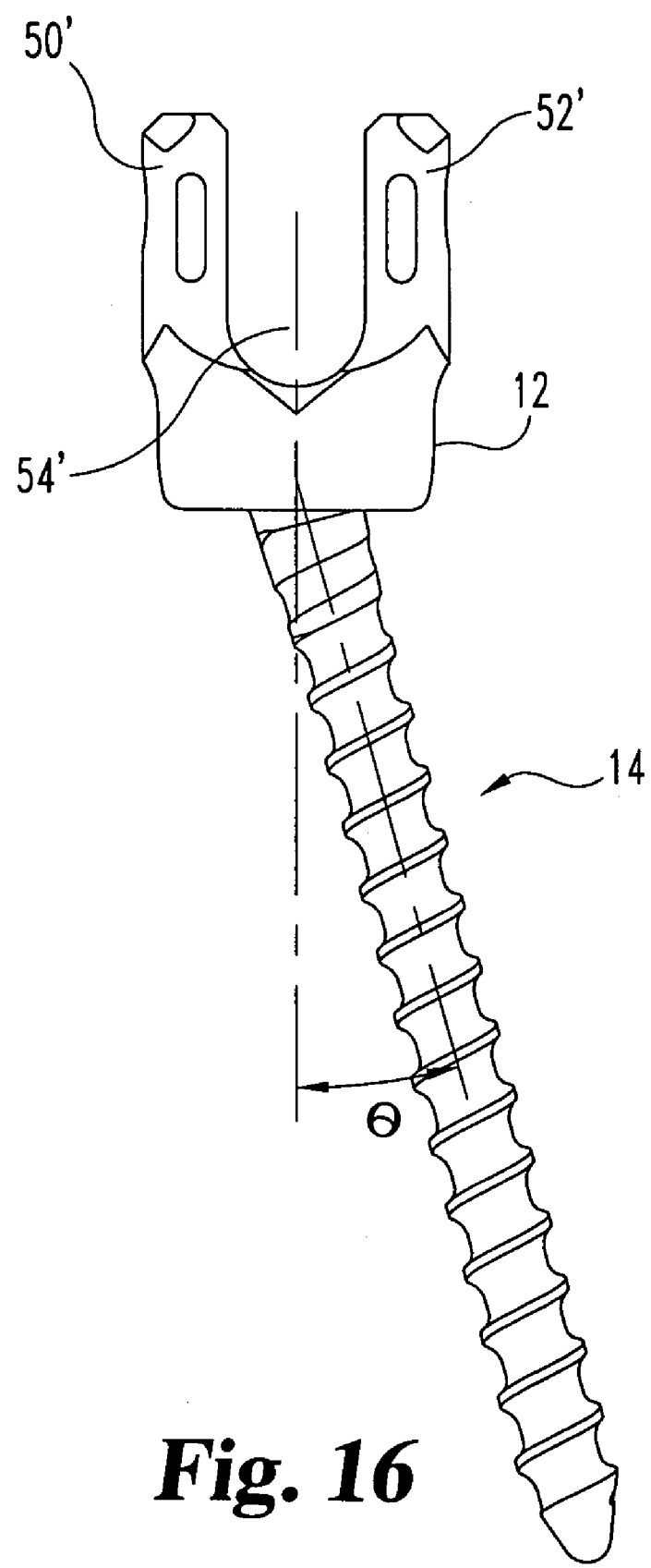
FIG. 16 is an elevational view of the embodiment shown in FIG. 14, rotated 90 degrees from the position in FIG. 14.

For example, the illustrated embodiment of assembly 10 shows an arrangement of surfaces 34a, 34b of receiver member 12 that will permit pivoting of anchor member 14 in a plane containing an axis through channel 54. That is, the illustrated embodiment of assembly 10 shows substantially cylindrically-shaped surfaces 32a and 32b below channel 54 and generally flat surfaces 34a and 34b below branches 50, 52. Surfaces 34a, 34b could be positioned elsewhere in receiver member 12 so that a plane in which anchor member 14 pivots is oblique or perpendicular to channel 54 and to an elongated member 20 in it. An embodiment is shown in FIGS. 14-16 in which anchor member 14 pivots substantially perpendicularly to channel 54' in receiver member 12', i.e. in a transverse plane, making an angle 0 with respect to a longitudinal axis of receiver member 12'. In that embodiment, internal geometry of receiver member 12' is rotated about 90 degrees from that of receiver members 12, 212 shown in FIGS. 1-3E and 8-13, e.g., substantially cylindrically-shaped surfaces are below channel 54' and generally flat surfaces are below branches 50', 52' In other respects, this embodiment of an assembly 10' is similar or identical to assembly 10 and parts previously shown and described. If an elliptical groove (similar to groove 46) and retaining member (similar to member 18) are used in assembly 10', the major diameter of the groove could be repositioned so as to be substantially parallel to the planes of one or more generally flat surfaces in receiver member 12', which may be comparable to surfaces 34a, 34b of receiver member 12.

Assembly 10' is used and assembled substantially as described above with respect to assembly 10. Assembly 10' can provide for certain orthopedic correction techniques, such as those described above with respect to inserting assembly 10 to a "pre-final" position. Once assembly 10' is inserted into a vertebra as desired, movement in a plane substantially along a rod (e.g. the sagittal plane) of receiver member 12' with respect to anchor 14 is substantially limited or prevented. Correction techniques useful in addressing trauma and/or degenerative conditions, such as compression, distraction, rotation and/or other adjustments of vertebrae or vertebral segments, can be applied to assembly 10' (or multiple assemblies 10', if they are used) or to bones. For example, if compression is desired, the surgeon may press assemblies 10' together with his or her fingers or with a tool (not shown). As another example, if distraction is desired, the surgeon may pull or push apart assemblies 10' with his or her fingers or with a tool (not shown). In either case, force applied to the sides of assemblies 10' will cause a change in relative position between assemblies 10', and will not substantially pivot receiver members 12' of assemblies 10' with respect to their respective anchors 14. An interbody device may be implanted between the adjusted vertebrae so as to maintain the desired spacing between the vertebrae. As previously noted, such operations on vertebrae, on one or more assemblies 10', or other orthopedic elements may be made as the surgeon desires and/or as dictated by a particular patient's condition.

As another example, embodiments of assembly 10 could be made without crown member 16. In such embodiments, surfaces 70 of head 66 of anchor 14 will be adjacent surfaces 34a, 34b of receiver member 12, and the relationship between surfaces 70 and 34a, 34b will limit pivoting of anchor 14 with respect to receiver member 12 to substantially one plane. Further, elongated member 20 would bear directly against head 66 in such embodiments.

As discussed above, several embodiments of the assembly have receiver members that are generally pivotable with respect to tissue or an anchor in such tissue in substantially one plane. That plane may be determined by the configuration of the assembly and/or by its positioning relative to tissue (e.g. a vertebra or other bone tissue). Surfaces within a receiver member of the assembly, surfaces on a crown member, and/or other features can be oriented so that an anchor and receiver member can pivot with respect to each other in a plane substantially parallel to the receiver member's channel, substantially perpendicular to the channel, or at any angle to the channel. The assembly can be connected to tissue so that the receiver member pivots substantially in one of an infinite number of planes, for example by rotating a screw-type anchor of an assembly into bone to a degree that produces pivoting substantially in a desired plane. With reference to a human body, such a plane may be substantially sagittal, substantially transverse, or may be between sagittal and transverse, or any other plane desired by the surgeon and permitted by the anatomy to be instrumented. An assembly in which the receiver member is pivotable with respect to an anchor, or tissue to which the anchor is connected, in a plane between a sagittal and a transverse plane can be useful in implant constructs in the lower vertebrae, sacral and/or iliac area, among other surgical situations or procedures.

What is claimed is:
1. An orthopedic medical apparatus comprising:
    a receiver member having a longitudinal aperture, a channel for receiving an elongated member transverse to said aperture, a lower opening, and a groove communicating with said longitudinal aperture, wherein a lower portion of said longitudinal aperture includes a pair of opposed substantially flat walls;
    a bone anchor member having a longitudinal axis and a head, said head having a substantially part-spherical portion and at least two substantially flat portions, said flat portions being substantially parallel to said axis and substantially parallel to each other, at least a portion of said head being in said aperture;
    a crown member having a rounded lower surface, a pair of opposite substantially flat external surfaces, and a pair of opposite substantially cylindrical external surfaces extending from one of said flat external surfaces to an opposite one of said flat external surfaces to provide said crown member with an oblong disc configuration, said crown member being placed in said aperture so that said lower surface is adjacent said head of said anchor member, wherein said pair of opposed substantially flat exter- nal surfaces are received in said longitudinal aperture adjacent said pair of opposed substantially flat walls of said receiver member; and a retaining member at least partially within said groove and around at least a portion of said anchor member; and wherein said flat portions are arranged substantially parallel to said substantially flat external surfaces of said crown member and are also arranged substantially parallel to said pair of opposed substantially flat walls defined by said lower portion of said longitudinal aperture.

2. The apparatus of claim 1, further comprising an elongated member at least partially in said channel.

3. The apparatus of claim 2, further comprising a compression member connected to said receiver member, wherein said compression member exerts compression on said elongated member.

4. An orthopedic medical apparatus comprising:
a receiver member having a longitudinal aperture, a channel for receiving an elongated member transverse to said aperture, a lower opening, and a groove communicating with said longitudinal aperture, wherein a lower portion of said longitudinal aperture includes a pair of opposed substantially flat walls;
a bone anchor member having a longitudinal axis and a head, said head having a substantially part-spherical portion and a pair of opposite flat portions, said flat portions being substantially parallel to said axis, at least a portion of said head being in said aperture;
a crown member having a rounded lower surface, a pair of opposite substantially flat external surfaces, and a pair of opposite substantially cylindrical external surfaces, said crown member being placed in said aperture so that said lower surface is adjacent said head of said anchor member, wherein said pair of opposed substantially flat external surfaces are received in said longitudinal aperture adjacent said pair of opposed substantially flat walls of said receiver member;
wherein said crown member includes a first opening extending laterally through one of said opposite flat external surfaces and a second opening extending laterally through the other of said opposite flat external surfaces, and wherein said pair of opposite flat portions of said bone anchor member are positioned at said first and second openings in said crown member and adjacent said pair of opposed substantially flat walls of said receiver member; and
a retaining member at least partially within said groove and around at least a portion of said anchor member; and
wherein said flat portions are arranged substantially parallel to said substantially flat external surfaces of said crown member and are also arranged substantially parallel to said pair of opposed substantially flat walls defined by said lower portion of said longitudinal aperture.

5. The apparatus of claim 1, wherein said receiver member channel has an axis substantially along which the elongated member runs, and wherein said anchor member is positioned with respect to said receiver member so that said anchor member is limited to pivotal movement with respect to said receiver member in substantially a single plane, said plane being one that substantially contains said channel axis.

6. The apparatus of claim 1, wherein said receiver member channel has an axis substantially along which the elongated member runs, and wherein said anchor member is positioned with respect to said receiver member so that said anchor member can pivot with respect to said receiver member in substantially a single plane, said plane being one that is substantially perpendicular to said channel axis.

7. The apparatus of claim 1, wherein said receiver member channel has an axis substantially along which the elongated member runs, and wherein said anchor member is positioned with respect to said receiver member so that said anchor member can pivot with respect to said receiver member in substantially a single plane, said plane being one that is substantially oblique to said channel axis.

8. An orthopedic medical apparatus, comprising:
a receiver member having an internal chamber with at least one substantially flat wall;
a crown member at least partially in said chamber, said crown member having a rounded lower surface, a substantially flat external side surface, and an opening extending laterally through said substantially flat external side surface; and
a bone anchor member having a longitudinal axis and head portion with at least one substantially flat wall portion, said head portion being adjacent said rounded lower surface of said crown member, said substantially flat wall portion of said anchor member being substantially parallel to said longitudinal axis and positioned at said opening in said crown member and adjacent said substantially flat wall of said receiver member, wherein said anchor member is limited to pivotal movement with respect to said receiver member in a single plane; and
wherein said chamber has two substantially flat walls that are substantially parallel to each other, said crown member having a pair of said substantially flat external side surfaces with one of said openings extending laterally through each of said substantially flat external side surfaces, wherein said opposite substantially flat external side surfaces of said crown member are positioned adjacent and substantially parallel with said substantially flat walls defined by said chamber of said receiver member, and wherein said head portion has two substantially flat walls that are substantially parallel to each other and which are positioned at said openings in said crown member and adjacent said substantially flat walls of said receiver member.

9. The apparatus of claim 8, further comprising an elongated member connected to said receiver member, wherein said elongated member does not contact said anchor member.

10. The apparatus of claim 9, wherein said flat wall of said receiver member is positioned so that said plane is one that substantially contains the portion of said elongated member within said receiver member.

11. The apparatus of claim 8, wherein said wall of said chamber has an elongated concave portion, and said crown member has a projection extending outwardly from said flat external side surface of said crown member, and wherein said projection fits slidably in said concave portion.

12. The apparatus of claim 8, wherein when said apparatus is implanted in a body, said plane is substantially a sagittal plane.

13. The apparatus of claim 8, wherein when said apparatus is implanted in a body, said plane is substantially a transverse plane.

14. The apparatus of claim 8, wherein when said apparatus is implanted in a body, said plane is substantially between a sagittal plane and a transverse plane.

15. The apparatus of claim 1, wherein said retaining member has an outer shape that is at least partially substantially oval, and said groove has a shape that is at least partially substantially oval, whereby relative movement of said retaining member in said groove is substantially limited.

16. The apparatus of claim 15, wherein said retaining member is one of substantially flat and undulated.

17. The apparatus of claim 1, wherein said crown member has a projection extending from each of said flat external surfaces, and wherein each said projection fits slidably in a recess formed along said longitudinal aperture in said receiver member.

18. The apparatus of claim 1, wherein said retaining member and said groove are each elliptical.

19. The apparatus of claim 18, wherein said elliptical groove has a major diameter that is generally parallel with said substantially flat walls of said receiver member.

20. The apparatus of claim 1, wherein said retaining member and said groove are each oval-shaped.

21. The apparatus of claim 20, wherein said oval-shaped groove has a major diameter that is generally parallel with said substantially flat walls of said receiver member.

22. The apparatus of claim 8, wherein said crown member has a pair of opposite substantially cylindrical external side surfaces each extending between said flat external side surfaces, said substantially flat external side surfaces each extending from a first of said substantially cylindrical external side surfaces to a second of said substantially cylindrical side surfaces to provide said crown member with an oblong disc configuration.

23. The apparatus of claim 15, wherein said substantially oval groove has a major diameter that is generally parallel with said pair of opposed substantially flat walls of said receiver member.

24. The apparatus of claim 15, wherein said retaining member and said groove each have an oblong oval shape.

25. The apparatus of claim 24, wherein said oblong oval shape of said groove has a major diameter that is generally parallel with said pair of opposed substantially flat walls of said receiver member.

26. The apparatus of claim 15, wherein said retaining member and said groove each have an elliptical shape.

27. The apparatus of claim 26, wherein said elliptical shape of said groove has a major diameter that is generally parallel with pair of opposed substantially flat walls of said receiver member.

28. The apparatus of claim 1, wherein said substantially flat external surfaces each extend from a first of said substantially cylindrical external surfaces to a second of said substantially cylindrical surfaces to provide said crown member with said oblong disc configuration.

29. The apparatus of claim 1, wherein said crown member includes a wall extending peripherally about an inner chamber, said wall defining said substantially flat external surfaces and said substantially cylindrical external surfaces, said head of said bone anchor member positioned within said inner chamber.

30. The apparatus of claim 1, wherein said rounded lower surface of said crown member includes a pair of opposing substantially flat inner surfaces that extend axially along said pair of opposite substantially flat external surfaces of said crown member.

31. The apparatus of claim 30, wherein said pair of opposing substantially flat inner surfaces of said crown member are positioned adjacent said flat portions of said anchor member.

32. The apparatus of claim 18, wherein said elliptical shape of said retaining member and said groove is oblong.

33. The apparatus of claim 20, wherein said oval-shaped retaining member and said oval-shaped groove are each oblong.

34. The apparatus of claim 4, wherein said substantially flat external surfaces each extend from a first of said substantially cylindrical external surfaces to a second of said substantially cylindrical surfaces to provide said crown member with an oblong disc configuration.

35. An orthopedic medical apparatus comprising:
a receiver member having a longitudinal aperture, a channel for receiving an elongated member transverse to said aperture, a lower opening, and a groove communicating with said longitudinal aperture, wherein a lower portion of said longitudinal aperture includes a pair of opposed substantially flat walls;
a bone anchor member having a longitudinal axis and a head, said head having a substantially part-spherical portion and at least one flat portion, said flat portion being substantially parallel to said axis, at least a portion of said head being in said aperture;
a crown member having a rounded lower surface, a pair of opposite substantially flat external surfaces, and a pair of opposite substantially cylindrical external surfaces extending from one of said flat external surfaces to an opposite one of said flat external surfaces to provide said crown member with an oblong disc configuration, said crown member being placed in said aperture so that said lower surface is adjacent said head of said anchor member, wherein said pair of opposed substantially flat external surfaces are received in said longitudinal aperture adjacent said pair of opposed substantially flat walls of said receiver member; and
a retaining member at least partially within said groove and around at least a portion of said anchor member; and
wherein said longitudinal aperture in said receiver member extends along a second longitudinal axis, said pair of opposed substantially flat walls in said lower portion of said aperture arranged generally parallel with said second longitudinal axis, said pair of opposite substantially flat external surfaces of said crown member and said flat portion of said bone anchor member also arranged generally parallel with said second longitudinal axis.

36. An orthopedic medical apparatus, comprising:
a receiver member having an internal chamber with at least one substantially flat wall;
a crown member at least partially in said chamber, said crown member having a rounded lower surface, a substantially flat external side surface, and an opening extending laterally through said substantially flat external side surface; and
a bone anchor member having a longitudinal axis and head portion with at least one substantially flat wall portion, said head portion being adjacent said rounded lower surface of said crown member, said substantially flat wall portion of said anchor member being substantially parallel to said longitudinal axis and positioned at said opening in said crown member and adjacent said substantially flat wall of said receiver member, wherein said anchor member is limited to pivotal movement with respect to said receiver member in a single plane; and
wherein said longitudinal aperture in said receiver member extends along a second longitudinal axis, said pair of opposed substantially flat walls in said lower portion of said aperture arranged generally parallel with said second longitudinal axis, said pair of opposite substantially flat external surfaces of said crown member and said substantially flat wall portion of said anchor member also arranged generally parallel with said second longitudinal axis.

* * * * *